United States Patent [19]

Nottingham et al.

[11] Patent Number: 4,991,441
[45] Date of Patent: Feb. 12, 1991

[54] POSITIONING ASSEMBLY FOR A TRANSDUCER IN A BORESONIC INSPECTION SYSTEM

[75] Inventors: Lawrence D. Nottingham, Charlotte, N.C.; Thomas E. Michaels; Jennifer E. Michaels, both of Freeville, N.Y.

[73] Assignee: Westinghouse Electric Corp., Pittsburgh, Pa.

[21] Appl. No.: 349,001

[22] Filed: May 8, 1989

Related U.S. Application Data

[62] Division of Ser. No. 160,211, Feb. 25, 1988, Pat. No. 4,864,862, Division of Ser. No. 117,918, Nov. 6, 1987, Pat. No. 4,757,516.

[51] Int. Cl.⁵ ............................................. G01N 9/24
[52] U.S. Cl. ........................................ 73/633; 73/634
[58] Field of Search ................ 73/622, 623, 633, 634, 73/644

[56] References Cited

U.S. PATENT DOCUMENTS

| | | | |
|---|---|---|---|
| 3,077,768 | 2/1963 | Allardt et al. | 73/634 |
| 3,780,571 | 12/1973 | Wiesener | 73/623 |
| 3,863,496 | 2/1975 | Hiramatsu et al. | 73/634 |
| 4,282,755 | 8/1981 | Gardineer et al. | 73/643 |
| 4,472,346 | 9/1984 | Takeda et al. | 73/633 |

Primary Examiner—Hezron E. Williams
Assistant Examiner—Louis M. Arana
Attorney, Agent, or Firm—D. C. Abeles

[57] ABSTRACT

An immersion base ultrasonic inspection system for interrogating the bore and near bore material of turbine and generator rotors by passing ultrasonic search units through the rotor bore. This system utilizes variable focus array inspection transducers in a shear mode inspection of the near bore material. The system includes a positioning assembly for a transducer which includes carriage means for supporting the transducer and a first positioning means for tilting one end of the carriage means in a radial axial plane whereby the transducer may be positioned at an angle to a longitudinal axis of the system. A second positioning means is provided for circumferentially rotating the transducer to a known and repeatable angular position. Position resolver means are coupled to the first and second positioning means.

5 Claims, 9 Drawing Sheets

POSITIONING ASSEMBLY FOR A TRANSDUCER IN A BORESONIC INSPECTION SYSTEM

CROSS REFERENCES TO RELATED APPLICATIONS

This is a divisional application of U.S. application Ser. No. 160,211 filed Feb. 25, 1988, now U.S. Pat. No. 4,864,862, which in turn is a divisional application of U.S. application Ser. No. 117,918, filed Nov. 6, 1987, now U.S. Pat. No. 4,757,516. This application is related to U.S. applications assigned to Westinghouse and entitles ULTRASONIC SIGNAL PROCESSING SYSTEM INCLUDING A FLAW GATE by the inventors of the invention described herein and having U.S. Pat. No. 4,803,638 and entitled BORE MAPPING AND SURFACE TIME MEASUREMENT SYSTEM by the inventors of the invention described and having U.S. Ser. No. 878,649. The above-mentioned applications are incorporated by reference herein. This application is also related to U.S. applications entitles APPARATUS FOR ULTRASONICALLY INSPECTING A LARGE SHAFT FROM A LIQUID-FILLED BORE and entitled WATER TREATMENT SYSTEM FOR ULTRASONIC INSPECTION OF TURBINE ROTORS FROM THE BORE having U.S. Pat. No. 4,699,008 and U.S. Pat No. 4,670,029, respectively.

BACKGROUND OF THE INVENTION

The present invention is directed to an inspection system for ultrasonically inspecting a material such as metal, and, more particularly, the present invention is directed to a boresonic inspection system which performs shear mode inspection of near bore material in turbine and generator rotors by passing ultrasonic search units through an axial rotor bore.

For many years, there has been increasing interest in, and a growing demand for, equipment and methods which can be used to inspect power generation turbine and generator rotors for possible material discontinuities or degradation which could lead to premature, and possibly catastrophic, failure of these components and which allow rotor life extension where appropriate. The consequences of a sudden, catastrophic failure of such a component would be severe, certainly in financial terms and possibly in terms of human losses. The center portion of the steel forgings from which these rotors are made, by the very nature of the manufacturing process, is perhaps the most suspect material in the rotor in terms of naturally occurring discontinuities and other material disorders. This is, in fact, one reason that a central bore hole is machined through most rotors in an attempt to remove this suspect material. In addition, the operating conditions at and near the central bore holes in rotors can lead to service related disorders such as thermal creep, fatigue and thermal embrittlement, especially in the presence of inherent forging discontinuities. Thus, there is a great interest in rotor inspection capabilities.

Several nondestructive test methods have been developed for use in interrogating the bore and near bore regions of rotor forgings. When the forging is new and before the final machining has take place, it is still cylindrical or near cylindrical in shape and ultrasonic inspection from the outside has proven to be a valuable tool. However, because of the complex geometries which characterize the outer peripheries of completely machined forgings, ultrasonic inspection from the outside is impractical for inspecting rotors once they are machined. Other methods such as visual and magnetic particle examination have been used successfully to inspect the bore, but these methods are only sensitive to discontinuities which intersect or are very near to the bore and then only yield a two dimensional view of the material and any detected discontinuities.

Since the early to mid 1970's, ultrasonic inspection from the rotor bore itself has gained fairly wide acceptance as viable volumetric inspection method. In this method, which has become known as boresonic inspection, the ultrasonic transducers are transported through the central bore hole by some convenient method and the ultrasonic beams are directed from the bore surface into the rotor material. The ultrasonic wave can penetrate well into the rotor material, and by collecting, processing, and observing any reflections of the wave which occur within the forging, one can get some idea of the integrity of the material. Volumetric inspection is achieved by scanning the transducers around the circumference and along the length of the bore while directing the ultrasonic beam into the material so that the beam has been ultimately passed through all of the material of interest.

Early boresonic test systems and some still in use, such as that described in U.S. Pat. No. 3,960,006, are based on conventional, contact ultrasonic practices.

More recently, a new direction regarding bore ultrasonic inspection of rotors has begun to emerge. A test system, known as TREES (Turbine Rotor Examination and Evaluation System) has been developed under the direction of the Electric Power Research Institute (EPRI) for the American Electric Power Company. This test system is the first known rotor bore inspection system to provide inspection capability based upon immersion ultrasonic testing techniques. For the purpose of this writing, TREES is categorized as a fixed focus immersion system.

Fixed focus immersion systems provide certain features which overcome many of the shortcomings of the contact systems. The transducers operate in an immersion bath which eliminates many, if not all, of the contact problems. No transducer shoes are required as the water provides a path for the sound to travel from the transducer to the rotor. The transducer can be offset from the bore by an amount which provides for the near field effects to occur entirely in the water so that the beam is formed and well behaved at the bore surface and beyond. Generation of either angled compressional or shear waves in the rotor can be easily accomplished by simply tilting the transducer such that the beam strikes the bore surface at other than normal incidence.

In the prior art, manual, pneumatic and motor driven inspection systems, the control systems that move the scan head and provide position indications have been cumbersome and inaccurate due to resolver locations that require knowledge of mechanical slack in the system and positioning apparatus that does now allow for high resolution positioning. As a result, the location and size of discontinuities and flaws have been inaccurately located. Inaccurate flaw location, requires that remachining to remove flaws cover a larger area than is necessary, weakening the rotor at its highest stress area, near the bore. Inaccurate flaw location also hinders comparison of previous inspections with current inspections because it is difficult to determine whether a given flaw is a new flaw or an old flaw that has been inaccurately located due to alignment inaccuracies.

See U.S. Pat. No. 4,757,716 for additional discussion relating to the background of this invention.

SUMMARY OF THE INVENTION

It is an object of the present invention to provide a mechanism which accurately positions immersion inspection transducers in a bore.

It is also an object of the present invention to provide motion axes which utilize radial displacement and rotation about a pivot to provide various combinations of surface time and refracted angle, in either a compressional or shear propagation mode.

It is an additional object of the present invention to provide two radial displacement motion axes for a transducer which will allow the transducer to be tilted for inspection of tapered bore areas.

It is another object of the present invention to provide a three axis motion system for positioning one or more transducers.

The present invention attains the above objects by providing an immersion based ultrasonic test system used to interrogate the bore and near bore material of turbine and generator rotors by passing ultrasonic search units through the rotor bore. This system utilizes variable focus array inspection transducers in a shear mode inspection of the bore surface and near bore material. A mapping transducer and a blind bore sensor allows the diameter of the rotor to be mapped as well as the end of a blind rotor to be detected. A scan head centering device or chuck deploys four radial arms to center and support the scan head. A transducer carriage is provided in the scan head that provides three axes of motion for the inspection transducer. The carriage provides position feedback to allow accurate transducer positioning throughout the rotor. The carriage also carries a ranging transducer that allows correction of inspection beam path geometry for varying bore diameters.

These together with other objects and advantages which will be subsequently apparent, reside in the details of construction and operation as more fully hereinafter described and claimed, reference being had to the accompanying drawing forming a part hereof, wherein like numerals refer to like parts throughout.

DESCRIPTION OF THE PREFERRED EMBODIMENTS

The present invention is a rotor ultrasonic inspection system which, based upon immersion ultrasonic test methods, utilizes variable focus shear waves generated by phased array transducers available from New York Institute of Technology. Shear waves are generally better at detecting interfaces that can be cracks in the rotor.

Figure 1:
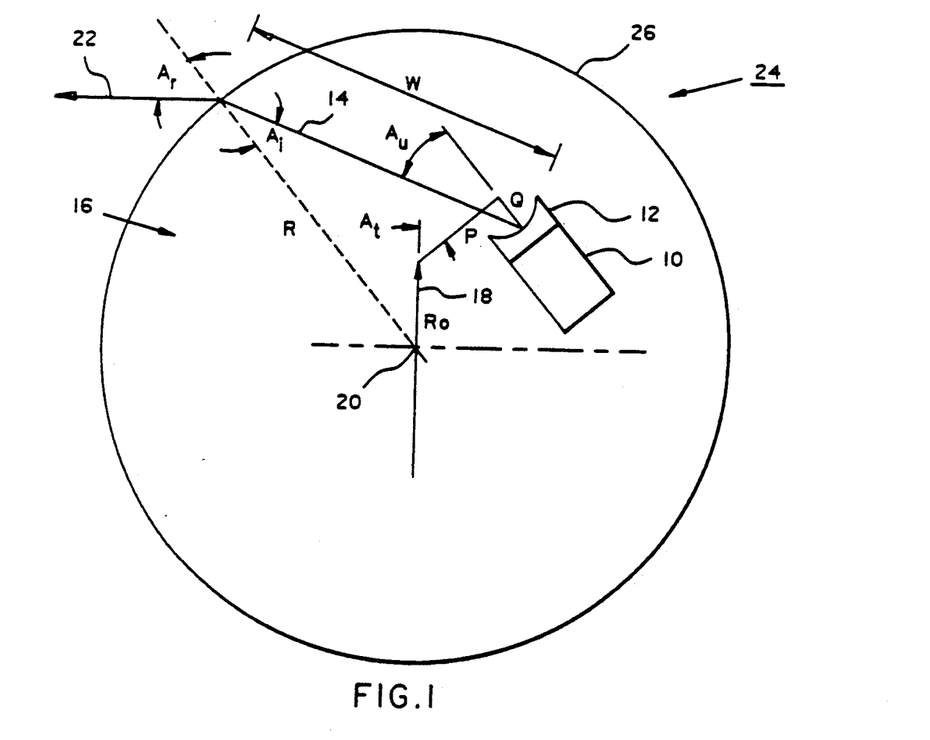
FIG. 1 depicts the relationship between an inspection transducer 10 and a rotor bore 24.

An understanding of the preferred transducer design is necessary to fully understand the present invention. Each transducer 10, as illustrated in FIG. 1, has nine elements that are concentric, planar arc segments, as in a section of an annular array (not shown). Each transducer 10 has a lense 12 attached to the front surface such that the emitted wave 14 passes first through the lense 12 and then into an immersion fluid 16. The lense 12 is designed such that the transducer operates at a specific offset from the bore centerline 20 and when operated at this point a refracted shear beam 22 of a specific angle is generated in the rotor material 24. Beam focus is achieved through a combination of two mechanisms. First, the lense 12 causes a diffraction of the beam as it passes through the complex, concave front surface of the lense 12 into the immersion fluid 16. Second, the pulsing of the array leads to constructive and destructive interference of the sound waves generated by the various elements and to the eventual formation of a high intensity focal spot. The lense 12 corrects for the effects of the cylindrical bore curvature and creates a geometrically focussed ultrasonic beam at a given depth in the rotor material 24. A geometrically focussed beam is one which is focussed primarily by the lense; that is, a beam that is formed by pulsing all of the elements at the same time. In this case, the geometric focal depth is approximately 1 to 1¼ inches radially below the bore surface 26 and the designed refracted angle Ar of the shear beam is approximately 40-60 degrees. The geometric focal depth and refracted ange are chose to allow steering of the beam to the bore surface in one direction and to a depth of 4-inches in the other direction. Other focal depths and refracted angles are possible and in certain cases are desirable.

The beam can be steered to, and focussed at, depths other than the geometric focal point by phasing the pulses applied tot he various array elements in a known manner. If, for example, it is desirable to steer and focus the beam nearer the bore surface, the outer element of the transducer is pulsed first and the others pulsed sequentially from the outer elements to the inner elements. The amount of the delay provided between each of the elements controls the degree to which the beam is steered, with more delay, steering and focussing the beam nearer the surface. If the beam is to be steered and focussed deeper than the geometric focal depth, the inner element is pulsed first and the sequential pulsing progresses toward the outer elements.

The steering and focussing of the beam by the phasing of the pulses applied to the various elements of the array is called transmit focus. In a real time inspection system, it is neither practical nor necessary to transmit focus on each reflector encountered. Because a given focal point has some depth of focus associated with it, a limited number of focal increments, with overlapping coverage at the transitions from one zone to the next, is sufficient. In the preferred embodiment four to six focal points providing four to six overlapping focal zones or windows is preferred when detailed inspections are necessary. In larger bores, the depth of focus is larger than in smaller bores, requiring less focal zones to get complete coverage in larger bores than in smaller bores.

A second form of focussing involves the method employed to receive the returning echoes. Receive focus is accomplished by receiving the reflected wave on more than one of the elements. For a given focal depth, specific amounts of delay are applied between the various elements receiving the returns so that the returns can be added in phase to achieve optimum signal enhancement. Continuous receive focus, as opposed to incremental receive focus, is achieved by applying appropriate delays to the return signals in hardware as a function of transit time such that the focussing is transparent to the operator. Continuous receive focussing is also referred to as dynamic focussing.

The present invention utilizes multi-element transmit focus with single element receive. This particular means of implementing the phase array technology was selected because of its capability in achieving the desired sensitivity with a minimum of system complexity. However, the present invention can utilize the above-discussed receive focus technique for higher accuracy if desired. Additional details concerning the use of the preferred transducers using the above-described methods can be obtained from the New York Institute of Technology or in the technical literature under the topic of medical ultrasonic imaging.

The present invention is an immersion system in which the bore is completely flooded with an immersion fluid and the transducers are not in contact with the bore. The present invention uses two transducers 10 to accomplish volumetric inspection, with focussed beams, over the first 4–6 inches of material from the bore surface 26 radially outward. The two transducers 10 are identical and each interrogates the full volume of material described. One transducer 10 (FIG. 1) is oriented relative to the bore such that the resulting beam in the material is in a radial/circumferential plane, oriented at an angle $A_r$ of 40–60 degrees from tangent, and aiming in the clockwise direction. The second transducer 10 is identical except that its beam is aimed in the counterclockwise direction. The transducers 10 are located relative to the bore such that the incident angle $A_i$ is about 19–26 degrees and the resulting 40–60 degree refracted wave 22 in the rotor propagates in the shear mode. The outer four array elements on each side of the transducer are used as transmit elements, and the center element is used as the receiver. This configuration permits the use of a single pre-amplifier near the transducer to boost the return signals before they travel over fairly long cables to the remote electronics.

Figure 2:
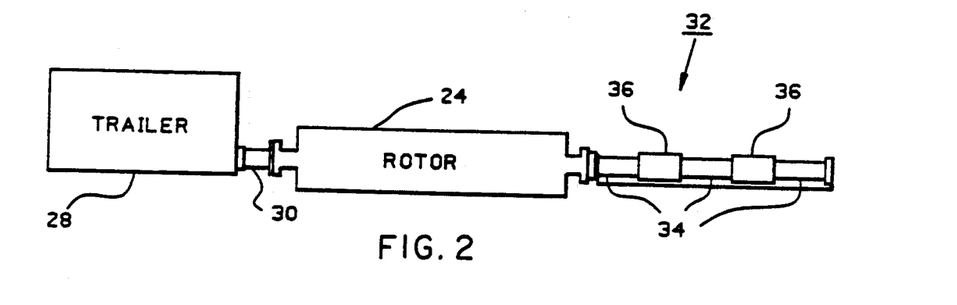
FIG. 2 illustrates the relationship between a rotor 24 being inspected and a trailer 28 housing part of the inspection system.

Part of the inspection system according to the present invention is housed in a trailer 28 coupled to the rotor 24 by a fluid carrying plexiglas tube 30, as illustrated in FIG. 2. On the opposite end of the rotor 24 from the trailer 28, is a scan head support unit 32 which includes fluid carrying tubes 34 and tube supports 36. The mating between the various fluid bearing tubes 34 and the rotor 24 is accomplished with adapter plates which tightly fit between the rotor and the tube, preventing immersion fluid escape using the necessary seals and O-rings appropriate to the rotor 24 being inspected. Although not shown in FIG. 2, the rotor 24 is tilted at approximately 6 inches per 20 feet (two degrees), with the end away from the trailer 28 being the lower end, so that the rotor bore is completely filled with the immersion fluid.

Figure 3:
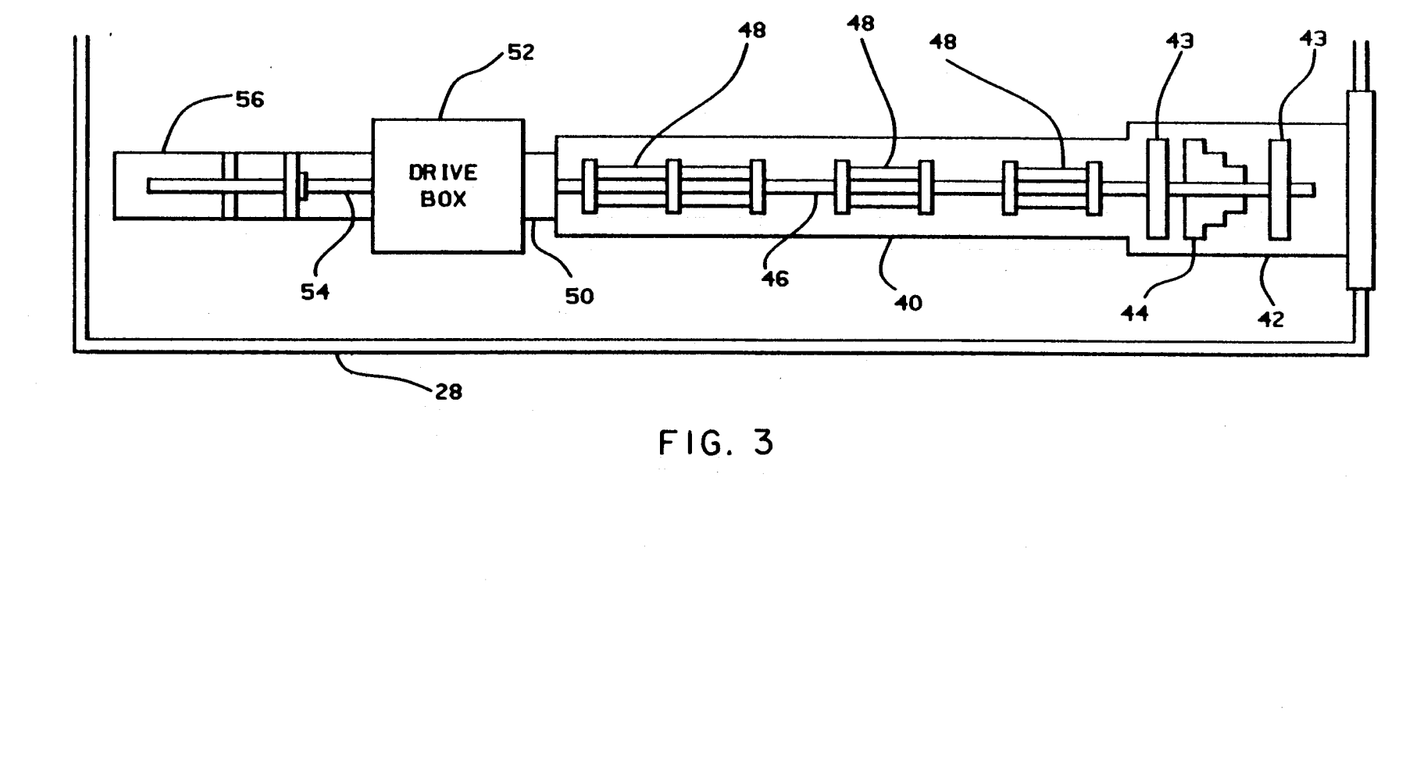
FIG. 3 is a top view of the interior of the trailer 28 of FIG. 2.

Inside the trailer, as illustrated in FIG. 3, is a tilted trough 40 also containing the immersion fluid. The entire trough 40 including calibration tank 42, drive box 52 and drive rod support trolley 56 are mounted on an I-beam 87 (FIG. 4) which is attached to the trailer 28 with jacks 89 and coupled to the trough 40, drive box 52 and calibration tank 42 by supports 88. The jacks 89 provide a means of tilting the trough 40 vertically moving the trough 40 horizontally to align the trough 40 assembly with the rotor, as described later. The tilting of the rotor ensures that the rotor is completely filled with immersion fluid and allows air in the rotor to escape without requiring additional air removal mechanisms. At one end of the trough 40 is a calibration tank 42 which contains a base for holding one or more calibration blocks 44 used to calibrate a scan head 46 prior to insertion into the rotor 24. Theses calibration blocks are constructed such that they have a positive positional reference such as a groove, for resting on a support structure 43 in the calibration tank 42 having a corresponding groove. This permits the use of various blocks for different bore diameters while maintaining positive and repeatable position reference for each block with respect to the position of the scan head 46. The scan head 46, while in the trough 40 is supported by slidably movable plexiglas support tubes 48 which are engaged by scan head chucks discussed in detail later. The support tubes 48 are supported by slide rails (not shown) in the bottom of the trough 40. At the end of the trough is a drive rod and seal 50 which prevents the immersion fluid in trough 40 from pouring into drive box 52 or into the trailer 28. The drive box 52 axially and circumferentially moves a segmented hollow rectangular geared drive rod 54 which is supported behind the drive box 52 by drive rod support trolley 56. The I-beam 87 also supports the trolley 56 although this feature is not shown in FIG. 4.

Figure 4:
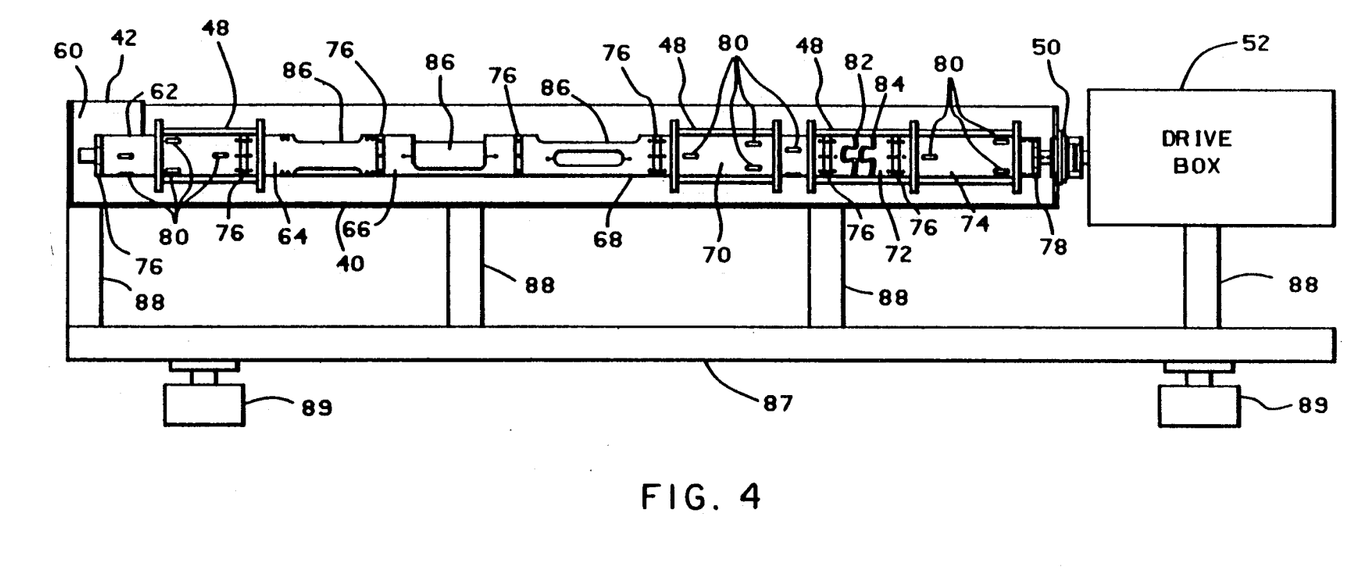
FIG. 4 is a detailed side view of the relationship between a trough 40 and a scan head 46 and a drive box 52.

The trough 40, drive box 52 and consequently the drive rod 54 are aligned with the tilted rotor by stretching piano wire from the center of the far end of the rotor 24 using a precision plug to hold the wire. The wire is stretched to and attached to a centering guide mounted at the midpoint of the trough 40. The trough 40 is then moved vertically and horizontally until the wire exits the rotor in the center. The trough 40 is then rotated around the midpoint until the wire is centered in an alignment guide mounted in the calibration tank 42. Proper alignment is necessary to prevent excessive twisting and bending of the drive rod 54 and scan head 46.

The cylindrical approximately three inch stainless steel scan head 46 is constructed of separate segments 60–74 which are jointed together by connectors 76 and is coupled to the drive rod by a circular-to-rectangular inner diameter fit adapter 78, as illustrated in FIG. 4. The connectors 76 and adapter 78 are constructed with no protruding surfaces so that the scan head 46 will not catch one the interior of a three inch diameter bottle bore. The scan head 46 is actually slightly less than three inches in diameter such that it will fit into bores as small as three inches in diameter.

The scan head 46 can have up to four transducer stations 60, 64, 66 and 68, where one station 64 is optional. The stations 64–68 are hollow stainless steel tubes with transducer cutouts 86. The required transducer stations 66 and 68 ar located between the two chuck stations 62 and 70. The transducer stations 66 and 68 are used for inspection transducers 10 under normal circumstances when the rotor bore extends through the entire length of the rotor 24 and the scan head 46 can pass out of the far end of the rotor 24. It is always advantageous to keep the transducers 10 as close together as possible axially since increased axial spacing equates directly to additional time required to pass the transducers through the bore.

The third required transducer station 60 is located forward of the front chuck station 62 and is used to hold an inspection transducer 10 when blind bore rotors or plugged rotors are inspected. In blind bore inspections, the scan head 46 cannot pass out the far end of the rotor 24 to carry the transducers 10 to the end. The inspection of a blind bore is first conducted in the normal manner over the length possible and then each inspection transducer is moved to the front station 60 and passed along the section missed during the normal portion of the test. The front station 60 during the normal part of the inspection carries bore mapping transducers, for mapping bore diameter as the scan head 46 is inserted into the rotor, as well as a blind bore end sensor for detecting the end of a blind bore. Bore mapping during insertion allows the chucks to be adjusted while moving the scan head 46 into the bore and later while moving the scan head 46 out of the bore during the inspection.

In addition to the two array inspection transducers at stations 60 and 68, the system contains additional single element ranging transducers located in each inspection station and used for surface tracking. These transducers are oriented such that their beams are directed radially outward with the bore surface reflection being the signal of interest. One of these ranging transducers is located in close proximity to each of the two array inspection transducers 10. They are used to track the bore surface as a function of circumferential and axial position and the measurements made with these transducers are used to correct the data collected with the array inspection transducers 10 for diameter changes, misalignment and other geometric variations. It is necessary to use separate transducers because the array transducers 10 do not receive a surface reflection when they are oriented to generate shear waves in the rotor 24. The relationship and operation of the inspection, ranging and bore mapping transducers are discussed in detail in the related applications mentioned in the cross references section.

The two required center transducer stations 66 and 68 each have three motor drive motions, as will be discussed in more detail later, which serve several functions during the course of an examination: (1) they are used to position the transducers properly within the scan head 46 during calibration such that the beam enters the material at the proper attitude; (2) they are used during a scan to reposition the transducer when a new bore size in encountered; and (3) they can be used to tilt the transducers 10 axially so that the beam is oriented properly as the transducer 10 passes through tapered bottle bore transitional regions The front transducer station 60, when carrying inspection transducers 10, normally has two motor driven motions which provide the same capabilities as the center stations excluding the axial tilt motion used in tapered regions. The front transducer station 60 can also contain an optional third motion to provide the axial tilt as well as an air evacuation probe. This probe is attached to a remote vacuum system via a vacuum tube which runs through the drive rod 54 and the scan head 46. The air evacuation probe can have one motor driven motion to move it radially outward toward the bore to remove entrapped air pockets, for example, from bottle bores.

Figure 5:
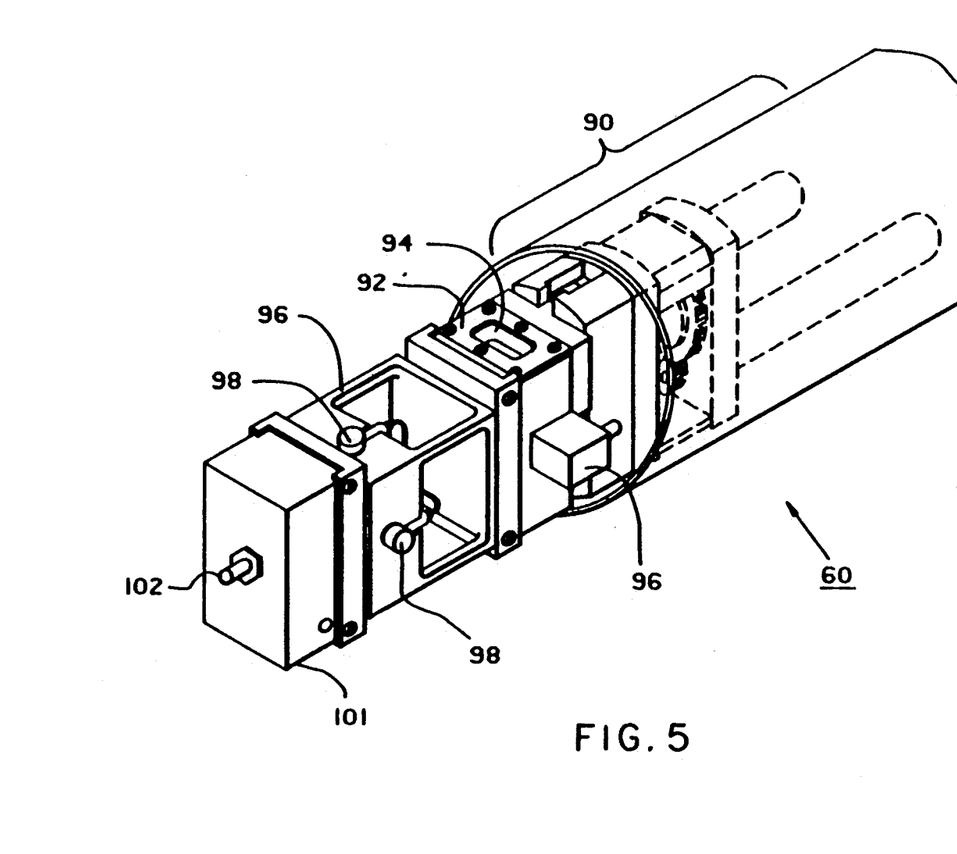
FIG. 5 is a perspective view of a front transducer station 60 when carrying bore mapping transducers 98 and a blind bore end sensor 100.

The front station 60 when carrying the bore mapping transducers and blind bore sensor, is configured as illustrated in FIG. 5. The assembly of FIG. 5 is rotated in alternating spiral motions during a mapping pass while the scan head 46 is being inserted into the bore. A radial motion assembly 90, which will be discussed in more detail later with respect to the inspection transducer carriage, provides radial motion to the mapping transducers 98 so that radial centering adjustments can be made if desired. Attached to the radial motion assembly is the vacuum chamber 92 which includes a vacuum port 94. The vacuum chamber 92 is coupled to a vacuum tube (not shown) by a vacuum tube fitting 96. The radial motion assembly 90 can move the vacuum port 94 into contact with air bubbles and allow them to be removed. Attached to the vacuum chamber 92 is a bore mapping fixture 96 which holds four bore mapping transducers 98, two of which are not shown in this perspective drawing. Suitable one-fourth inch diameter piezoelectric ceramic transducers are available from Panametrics of Massachusetts. The bore mapping transducers 98 are held in position by set screws in fixture 96. The fixture 96 points the transducers 98 normal to the bore surface 26 while the radial assembly 90 centers the fixture 96. The electrical wires from the bore mapping transducers 98, since the entire assembly is in the immersion fluid, should be water tight. On the front of the bore mapping fixture 96 is a blind bore sensor switch 100 with a switch plunger 102. When the blind bore plunger 102 is depressed, the axial motion drive assembly is immediately disabled for continued forward motion of the scan head 46 into the bore. If an inspection transducer 10 is substituted for the bore mapping transducers 98, a tilting mechanism, which will be discussed in more detail later with respect to the inspection transducer carriage, is substituted for the bore mapping fixture 96.

Figure 6:
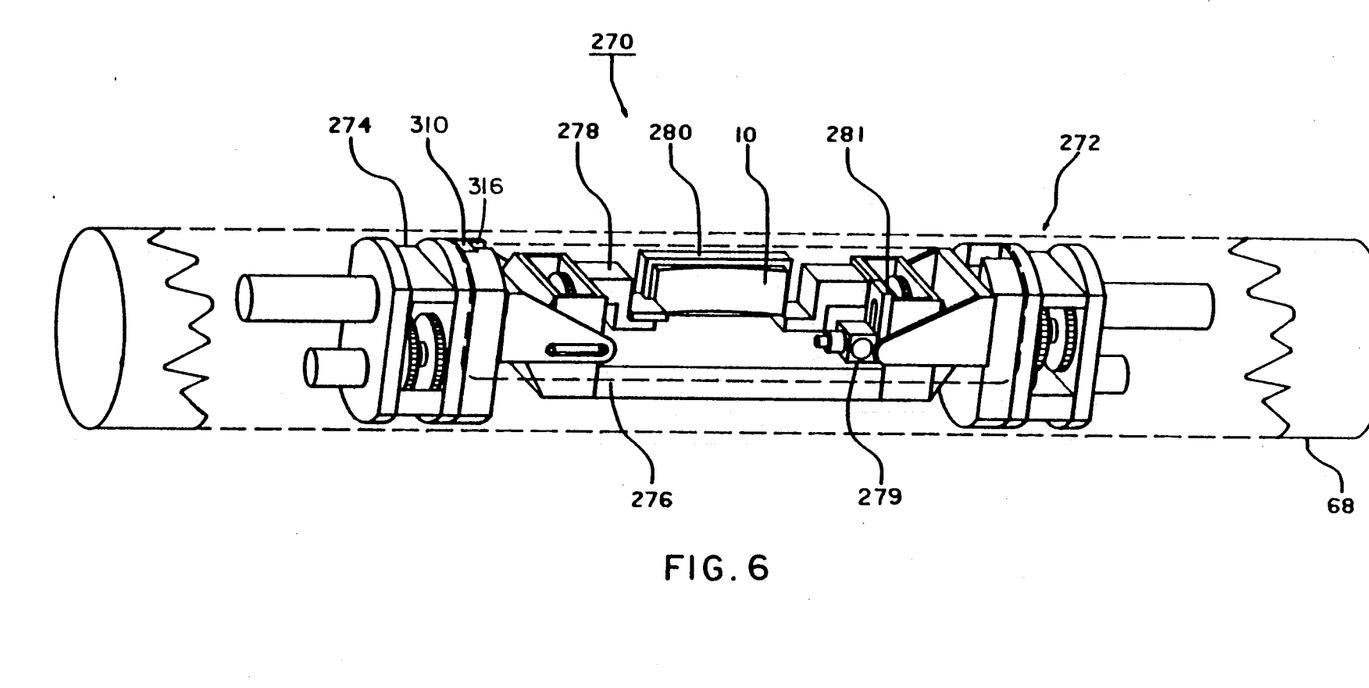
FIG. 6 is a perspective view of a carriage 270 for an inspection transducer and a ranging transducer 278 as positioned in the scan head 46.

Each of the inspection transducers 10 is mounted in a carriage which has three independent motion axes to properly position the transducer 10 such that the ultrasonic beam enters the material at the proper incident angle. Radial support assemblies 272 and 274, as illustrated in FIG. 6, provide radial adjustment of the transducer and when one radial support assembly is held at a constant level, while the other radial support assembly is moved, the transducer can be tilted. The carriage 276 attached to the radial support assemblies 272 and 274 can be used to rotate the transducer support bar 278 providing the third axis of motion. The transducer carriage also holds a ranging transducer 279 on an adjustable bracket 281.

In immersion ultrasonic testing the key parameters which must be controlled in order to maintain beam integrity are water path length, or transducer standoff distance, and incident angle, or the angle at which the beam strikes the bore surface 26. Water path length important since reflector positions must be is determined by a calculation based on the wave transit time in combination with a knowledge of the beam path and associated travel velocities. When focussed beams are used, water path length is even more significant because if affects the point within the material at which the beam will be in focus. The incident angle is important since it affects the beam propagation mode in the material (i.e., compressional mode or shear mode), its refracted angle in the material, and the intensity of the beam. All of these play key roles in maintaining inspection sensitivity, resolution, and accuracy of positional placement of reflectors. In the preferred embodiment, the transducers 10 are placed relative to the bore surface 26 such that the resultant wave in the rotor material propagates in shear mode, in a radial-circumferential plane, and at a refracted angle of about 45 degrees relative to tangent. The transducer offset and the resulting water path lengths are a matter of transducer design and can be set to any desired value.

FIG. 1 shows the key transducer position parameters for immersion based, shear mode interrogation of rotor material with the ultrasonic beam entering from the bore. The angle $A_u$ at which the ultrasonic beam exits from the transducer 10 is fixed for a particular transducer 10 by the transducer 10 and lense 12 designs. The desired refracted angle $A_r$ in the rotor material and the desired water path length W which the transducer must be offset from the bore surface 26 are determined by the transducer design. The key to achieving sensitive, accurate, repeatable inspections is to correctly position the transducer 10 relative to the bore surface so that the water path length W and the refracted angle $A_r$ are accurately set to the design values and can be repeated accurately. FIG. 1 also shows the two motion axes used in the present invention to properly position the transducer 10. The offset $R_o$ is the radial support motion and the angle $A_t$ is the transducer tilt motion. The transducer 10 offsets P and Q are setup values which are functions of the position in which the transducer 10 is mounted within the support carriage 276. During the process of mounting the transducer 10, the values for P and Q are fixed and can be measured with a mechanical measuring device, and the transducer 10 is also adjusted so that the beam is in a radial-circumferential plane, that is, the transducer 10 is adjusted sot hat it is not tilted axially. The values set for radial offset $R_o$ of the rotation axis and transducer tilt $A_t$ about the rotation pivot point are servo-motor driven and the positions are read by resolvers and fed back to a central computer for motion control and operator display. The water path W and refracted $A_r$ angle can be calculated according to the following equations:

$$C = (R_o \sin A_t - Q)\tan A_u + P + R_o \cos A_t$$

$$A_i = \sin^{-1}[(C/R) \cos A_u]$$

$$W = C \sin(90° - A_u - A_i)/\sin A_i - (R_o \sin A_t - Q)/\cos A_u$$

$$A_r = \sin^{-1}[(V_s/V_w)\sin A_i]$$

where, as illustrated in FIG. 1, $A_r$ equals the refracted angle in shear mode, $A_i$ equals the incident angle, $A_u$ is the ultrasonic beam angle out of transducer 10, $A_t$ is the transducer 10 rotation angle, Q equals the fixed offset of the transducer 10 from the center of the transducer tilt rotation in a direction parallel or nearly parallel to the beam, P is the fixed offset of transducer 10 from center of the transducer tilt rotation in a direction perpendicular or nearly perpendicular to the beam, R is the bore radius, $R_o$ equals the radial offset of the transducer rotation axis, W is the water path length (the immersion fluid path length), $V_w$ is the velocity of sound in water, and $V_s$ is the shear velocity in steel. The transducer 10 is clamped in a mounting bracket 280 which is part of the transducer carriage 276. The bracket and support arm 278 can be rotated within the carriage 276 which results in transducer rotation $A_t$. The entire carriage 276 is displaced radially to accomplish the second motion $R_o$ required for transducer positioning.

Figure 7A:
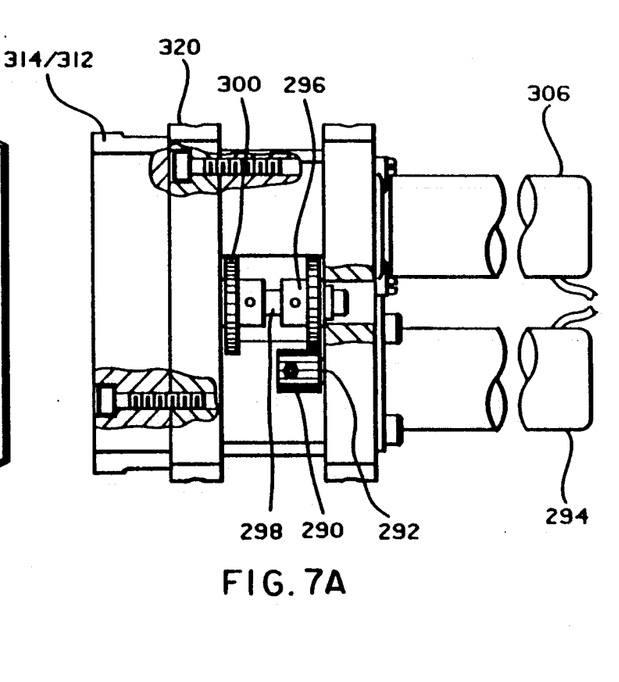
FIGS. 7A-7C illustrate details of the radial motion assembly.
Figures 7B, 7C:
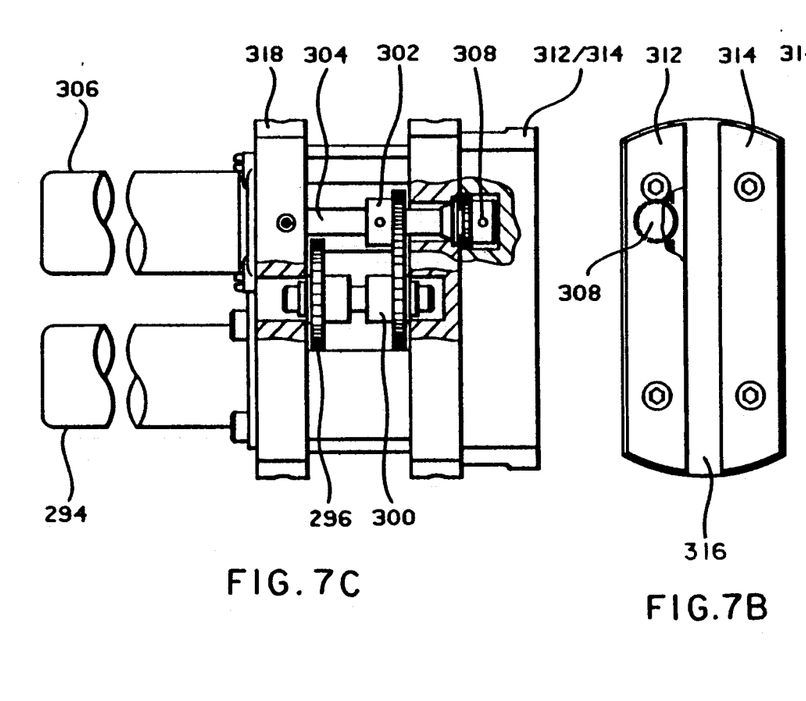

The radial motion at each end of the transducer carriage 276 is accomplished by the radial motion assembly, shown in FIGS. 7A-7C. The assembly is designed to mount inside the cylindrical stainless steel scan head 46. All components fit within a limited portion of the cross section of the scan head 46 so that additional space is reserved for wiring which must pass by the radial support (see end view FIG. 7B). A drive gear 290 is mounted on a shaft 292 of a drive motor 294 (FIG. 7A). The drive gear 292 engages with spur gear 296 which is mounted on an intermediate shaft 298. Gear 300, which is also mounted on the intermediate shaft 298, engages spur gear 302 mounted on the output shaft 304 (FIG. 7C). This output shaft 304 directly drives a position resolver 306 at a 1 to 1 ratio and has a second gear 308 which runs a rack 310 in a radial direction. The rack 310 is T-shaped and is part of a carrying bracket that supports the carriage 276. Each shaft is provided with the appropriate bearings to ensure smooth operation.

The T-shaped gear rack 310 slides in rack guides 312 and 314 (FIG. 7B) which support it and maintain it in intimate contact with gear 308 which drives the rack 310. The guides 312 and 314 form a T-shaped channel 316 (FIG. 6) which securely supports the rack 310 throughout its length. The gear rack 310 is attached to the end of the transducer carriage bracket so that operation of the radial support motor results in a radial displacement of the end of the carriage 276. Two of the radial support assemblies are used, one attached to each end of the carriage, to support the carriage 276 and provide for axial tilt. The gear racks 310 are interchangeable and are made in different lengths to cover different bore sizes. Appropriate spacers are provided to maintain separation between mounting plates 318 and 320 for holding the motor 294, resolver 306 and guides 312 and 314.

The radial offset of the transducer 10 rotation axis is controlled by the two radial motion assemblies 272 and 274, one located each axial end of the transducer carriage 276, so that the two radial motions can be used to tilt the transducer carriage 276 in the radial-axial plane as the transducer 10 passes through tapered areas of a bore. If this tilting capability is to be used for tapered areas in this manner, the transducer can be manually tilted in the mounting bracket 280 (rotation about its radial axis) to maintain the beam in a plane which is perpendicular to the bore surface. This adjustment, if required, is done during system calibration. Alternately, transducer 10 rotation about its radial axis could be incorporated as a fourth motion. As still another option, and the preferred one, the carriage is tilted through the use of the two radial supports, and any reflector positional error which results from not providing the accompanying rotation about the radial axis of the transducer would be removed using known geometry calculations with parameters that are determined during calibration.

Figure 8A:
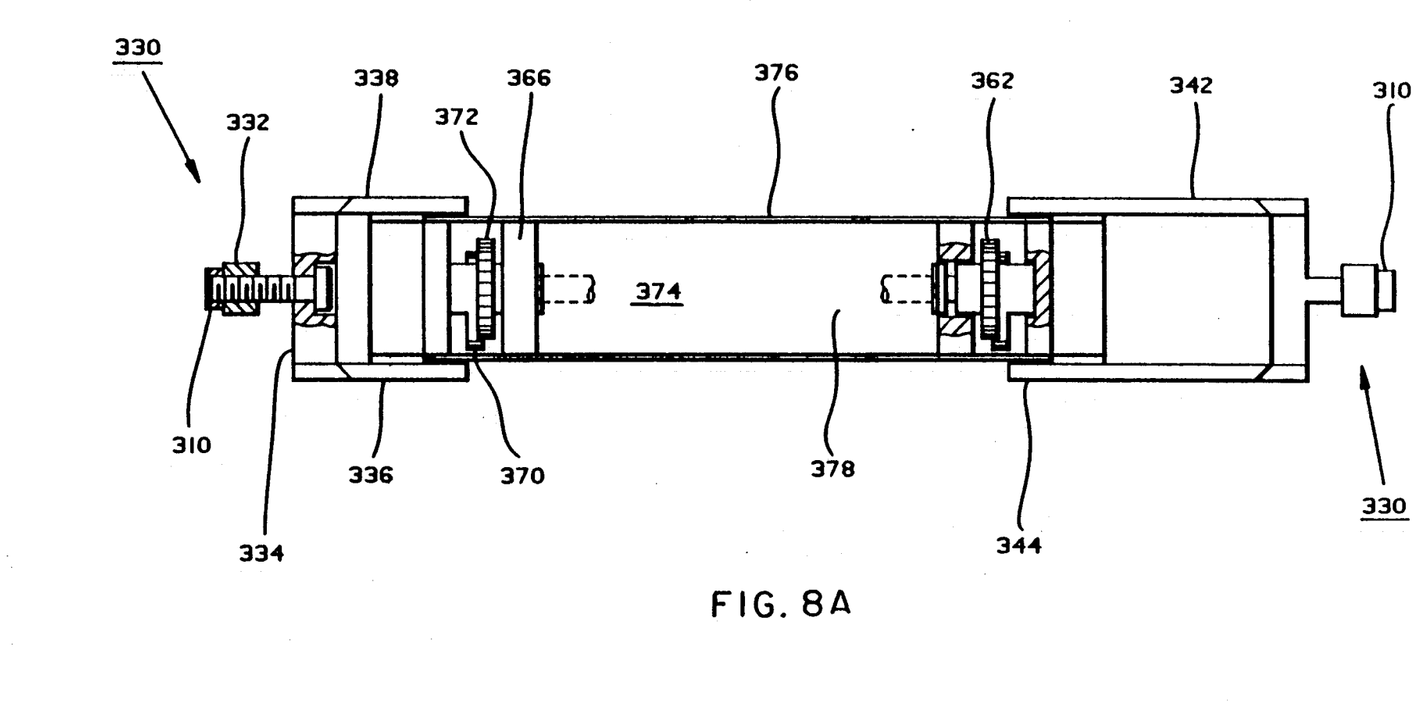
FIGS. 8A-8E depict the components of the carriage assembly.
Figure 8B:
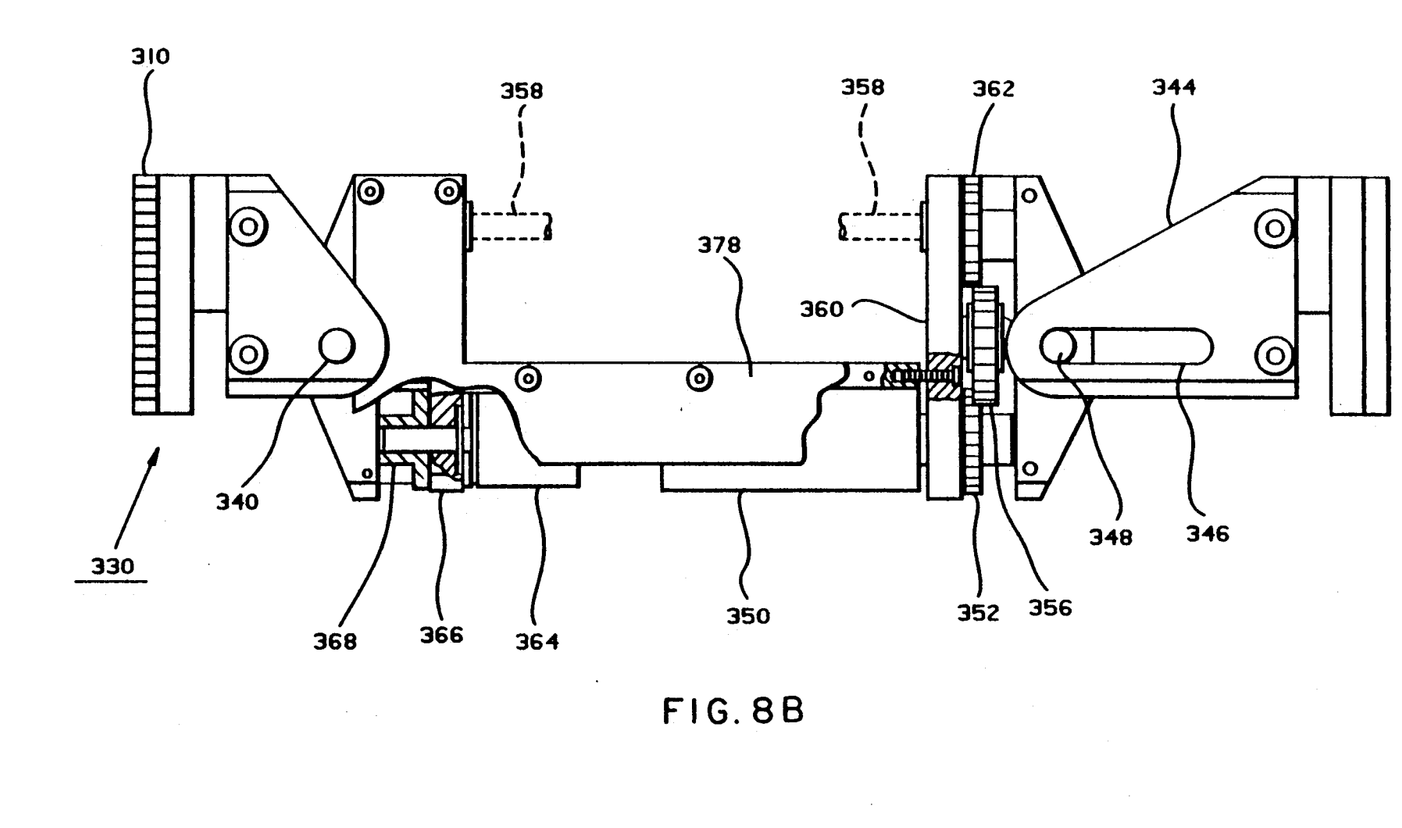
Figure 8C:
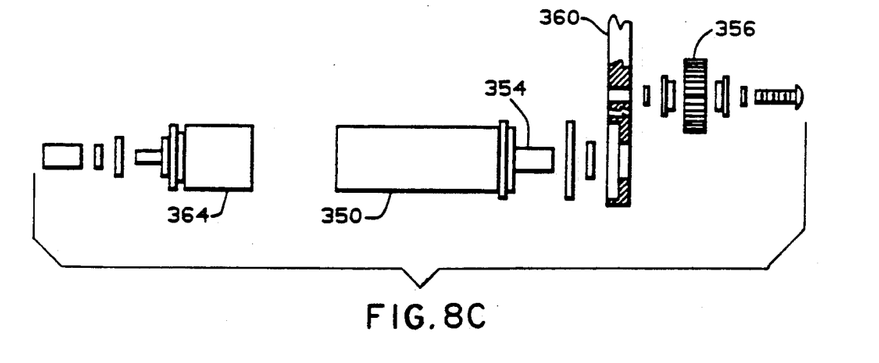

The transducer carriage 276 is shown in detail in FIGS. 8A-8C. Each gear rack assembly 330 is made up of the gear rack 310, a spacer 332 which positions it properly relative to the gear 308 which drives it, a mounting plate 334 to which the gear rack 310 and spacer 332 are attached, and two side plates 336 and 338 which attach to the mounting plate 334 and to the carriage and form the carriage mounting bracket. The side support plates 336 and 338 are rigidly attached to the gear rack mounting plate 334 and to the carriage 276 via a pivot shaft 340. The side or pivot plates 336 and 338 on one end of the carriage 276 provide only rotation, and the pivot plates 342 and 344 on the other end of the carriage 276 provide for axial motion of the carriage relative to the pivot plates as well as rotation. This is accomplished through the use of a sliding pivot slot 346 in each plate and allows for the effective change in the axial dimension of the carriage 276 by sliding on pivot shaft 348, which goes by the cosine of the tilt angle, as it is tilted.

The carriage assembly which holds and rotates the transducer mounting fixture, is shown in a cutaway view of FIG. 8B. A motor 350 lies in the bottom portion of the aluminum carriage 276, with its axis parallel to the transducer rotation axis, and with its drive end facing outboard rather than toward the center of the carriage 276. The motor 350 has an integral gear box and is available from TRW Corporation through distribution of their TRW Globe motor products. A drive gear 352 is mounted on the motor shaft 354 and drives an intermediate gear 356 which is used merely to increase the spacing between the motor 350 and the transducer rotation shaft 358 without using large gears. The motor 350, intermediate gear 356 and shaft 358 are mounted on a motor plate 360 forming one end of the carriage 276. The intermediate gear 356 engages gear 362 to rotate the transducer rotation shaft 358. The transducer rotation shaft 358 is directed back over the motor so that transducer lies above the motor. A resolver 364 is mounted in resolver mounting plate 366 in line with the motor 350 and transducer rotation shaft 358, to the second part of transducer rotation shaft 358. The carriage also includes a center plate 374 and two side plates 376 and 378 which form a U-shaped rigid structure for carrying the transducer 10.

Figure 8D:
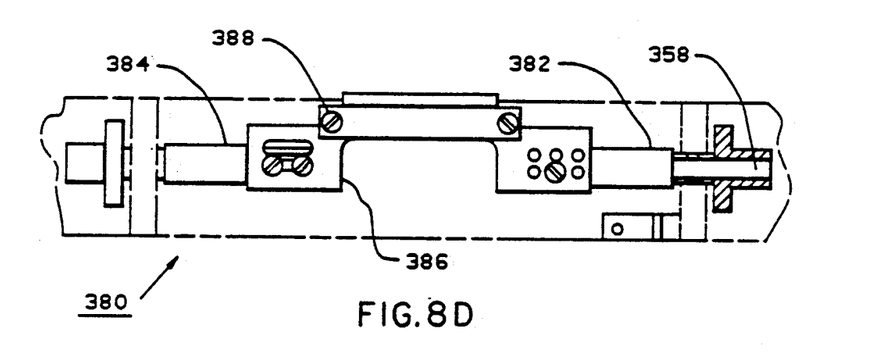
Figure 8E:
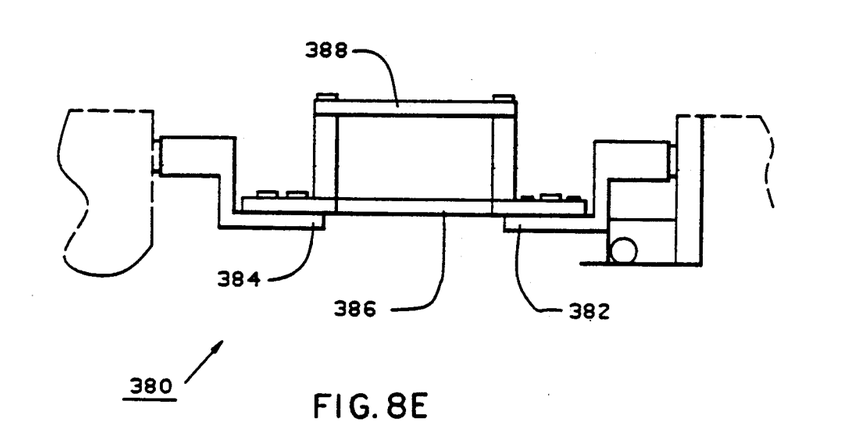

A transducer mounting bracket assembly 380 (FIGS. 8D and 8E) attaches to the shaft 358. The mounting bracket assembly includes shaft riders 382 and 384 which support an adjustable transducer holder 386 having a cutout that prevents ultrasonic reflections from the holder itself. Other artifact reflections discovered during calibration can be damped with appropriate damping material. The transducer 10 is held in holder 386 by a top plate 388. Motor rotation is converted to a rotation of the transducer mounting bracket, which is transferred to the resolver gearing, and finally to the resolver 364 for position readout and monitoring. The space between the motor 350 and resolver 364 and the transducer rotation shaft 358 is sufficient to allow the transducer 10 to rotate without interfering with the rest of the carriage 276. All shafts are provided with appropriate bearings to allow smooth operation.

The normal configuration for the front station 60 during blind bore inspections is to attach a modified carriage to the front radial support motion. This modified carriage (not shown) is similar to the normal carriage shown in FIGS. 8A–8E except the end plates are removed from both ends of the carriage and one end is rigidly attached to rack assembly 330. One optional modification to this inspection type front station is to insert a manual tilt motion between the rack assembly and the modified carriage to provide for tilting of the carriage during inspection of tapered regions. This tilt motion could also be motor driven with a resolver readout.

Suitable motors, resolvers, gears and bearings for the transducer station can be obtained from the suppliers previously mentioned.

Descriptions of additional components of the present invention can be found in U.S. Pat. No. 4,757,716.

The many features and advantages of the invention are apparent from the detailed specification and thus it is intended by the appended claims to cover all such features and advantages of the invention which fall within the true spirit and scope thereof. Further, since numerous modification and changes will readily occur to those skilled in the art, it is not desired to limit the invention to the exact construction and operation illustrated and described and accordingly, all suitable modifications and equivalents may be resorted to, falling within the scope of the invention.

What is claimed is

1. A positioning assembly for a transducer in an ultrasonic inspection system comprising:
    carriage means for supporting said transducer;
    a first positioning means for tilting one end of said carriage means in a radial axial plane whereby said transducer may be positioned at an angle to a longitudinal axis of said inspection system;
    said first positioning means comprising a gear rack and means coupled hereto for moving said gear rack;
    a second positioning means for circumferentially rotating said transducer to a known and repeatable angular position; and
    position resolver means coupled to said first and second positioning means.

2. A positioning assembly as recited in claim 1, wherein said first positioning means further includes a rack slide in which said gear rack is mounted for movement and said means for moving said gear rack includes a gear coupled to said gear rack and a first motor coupled to said gear.

3. A positioning assembly as recited in claim 1, which includes a fixture mounted on said carriage means for supporting said transducer, and said second positioning means includes a rotatable shaft coupled to said fixture and a second motor coupled to said shaft.

4. A positioning assembly for a transducer in an ultrasonic inspection system comprising:
    a carriage;
    a fixture mounted on said carriage for supporting said transducer;
    a first positioning means coupled to a first end of said carriage for tilting said first end of said carriage in a radial axial plane whereby said transducer may be positioned at an angle to a longitudinal axis of said inspection system;
    said first positioning means comprising a gear rack mounted for movement in a rack slide, a gear coupled to said rack and a first motor coupled to said gear;
    a first positioning resolver coupled to said first positioning means;
    a second positioning means for circumferentially rotating said transducer to a known and repeatable angular position;
    said second positioning means comprising a rotatable shaft coupled to said fixture and a second motor coupled to said shaft; and
    a second position resolver coupled to said second positioning means.

5. A positioning assembly as recited in claim 4, wherein a second end of said carriage is pivotally and axially slidably mounted in a pivot slot.

* * * * *